US008864782B2

(12) United States Patent
Whitehouse

(10) Patent No.: US 8,864,782 B2
(45) Date of Patent: Oct. 21, 2014

(54) OPHTHALMIC MARKING DEVICE

(76) Inventor: Geoffrey Mark Whitehouse, Forster (AU)

(*) Notice: Subject to any disclaimer, the term of this patent is extended or adjusted under 35 U.S.C. 154(b) by 703 days.

(21) Appl. No.: 13/002,668

(22) PCT Filed: Jun. 16, 2009

(86) PCT No.: PCT/AU2009/000756
§ 371 (c)(1),
(2), (4) Date: Feb. 3, 2011

(87) PCT Pub. No.: WO2010/003169
PCT Pub. Date: Jan. 14, 2010

(65) Prior Publication Data
US 2012/0197278 A1 Aug. 2, 2012

(30) Foreign Application Priority Data
Jul. 9, 2008 (AU) .................. 2008903531

(51) Int. Cl.
*A61F 9/00* (2006.01)
*A61F 9/013* (2006.01)
*A61B 19/00* (2006.01)
*A61B 17/3209* (2006.01)

(52) U.S. Cl.
CPC .......... *A61F 9/0136* (2013.01); *A61B 2019/545* (2013.01); *A61B 17/32093* (2013.01)
USPC ....................................... 606/166

(58) Field of Classification Search
CPC ..... A61F 9/007; A61F 9/00754; A61F 9/013; A61F 9/0133; A61F 9/0136
USPC ................. 606/107, 116, 166, 186
See application file for complete search history.

(56) References Cited

U.S. PATENT DOCUMENTS

| | | | |
|---|---|---|---|
| 4,417,579 A | 11/1983 | Soloviev et al. | |
| 4,739,761 A | 4/1988 | Grandon | |
| 4,880,017 A | 11/1989 | Soll et al. | |
| 6,217,596 B1 | 4/2001 | Farah | |
| 2007/0239183 A1 | 10/2007 | Melki | |
| 2009/0254108 A1* | 10/2009 | Davis ........................... 606/166 | |

FOREIGN PATENT DOCUMENTS

DE 202008004593 U1 6/2008

OTHER PUBLICATIONS

PCT/AU2009/000756 filed Jun. 16, 2009, Intl. Search Report & Written Opinion dated Aug. 24, 2009 (7 pages).
Supplementary European Search Report dated May 27, 2011 of European Appl. No. 09793695.9 filed Jun. 16, 2009 (5 pages).

* cited by examiner

*Primary Examiner* — Ashley Fishback
(74) *Attorney, Agent, or Firm* — Pillsbury Winthrop Shaw Pittman LLP

(57) ABSTRACT

An ophthalmic marker having a U-shaped yoke at one end of a cranked axle is disclosed. The axle is rotatable mounted with a co-axial cylindrical handle. The other end of the axle extends beyond the handle and is bifurcated. A plumb bob having a sphere and a stem is pivotally mounted on the bifurcated end of the axle. The yoke has three marker points the upper two of which are maintained in a horizontal plane by a gravitational force urging the plumb bob into a vertical plane notwithstanding the handle not being held exactly horizontal. A method of eye marking and marker making are also disclosed.

4 Claims, 4 Drawing Sheets

OPHTHALMIC MARKING DEVICE

CROSS-REFERENCE TO RELATED APPLICATIONS

This is the U.S. National Stage of PCT/AU2009/000756 filed Jun. 16, 2009, which claims priority to Australian Application No. 2008903531 filed Jul. 9, 2008, the entire contents of both applications which are incorporated herein by reference in their entireties.

FIELD OF THE INVENTION

The present invention relates to optical equipment and, in particular, to a marking device used by an ophthalmic surgeon to mark a patient's eye prior to, for example, intraocular surgery such as cataract surgery.

BACKGROUND ART

Cataract surgery has been performed for many years. Toric intraocular lenses have been available for many years (Star-Surgical/Rayner) but recently Alcon has popularised their use. This lens is particularly useful for patients having astigmatism. Roughly one third of all patients requiring cataract surgery have astigmatism and in order for the intraocular lens to function correctly it must be accurately placed. It is estimated that for every degree of incorrect orientation, the astigmic correction factor for such an intraocular lens decreases by approximately 3%. As a consequence, pre-operative marking is imperative for accurate surgery.

However, measurements on the patient's eye which are conducted pre-operatively are conducted in the consulting rooms of the ophthalmic surgeon where the patient sits upright with his torso in a vertical position. However, when the patient lies down, and is thus supine as required for surgery, the eye rotates by a variable amount which differs considerably from patient to patient. Thus the intention of the marking procedure is to enable the eye to be marked with reference markings which can be used to determine the correct alignment of the intraocular lens, the correct alignment of incisions, etc., during surgery. The marks themselves are made with a dye that is painted onto or otherwise applied to various prongs of the marker and which are accurately pressed onto the eye whilst the patient is seated and thus has his head vertical.

There are three basic prior art marking devices. One class of such devices are free hand systems where the marking prongs are located at one end of an elongate stem or pencil like handle which is held by the ophthalmic surgeon. This relies upon the dexterity of the surgeon. There is another device which incorporates a small spirit level into the handle in order to indicate a horizontal plane. There is a third class of markers which incorporate a plumb bob and thus rely upon gravitational forces to maintain the marking device aligned with the vertical. It is with this class of marking devices that the present invention is concerned. The particular prior art device which gave rise to the present invention is manufactured by Rumex of St Petersburg, Fla., USA.

GENESIS OF THE INVENTION

The genesis of the present invention is a desire to improve the abovementioned Rumex prior art marking device.

SUMMARY OF THE INVENTION

In accordance with a first aspect of the present invention there is disclosed an ophthalmic marker for marking a patient's eyeball prior to intraocular surgery, said marker comprising central longitudinal axle contained within, and rotatable relative to, a substantially co-axial substantially cylindrical body, one end of said axle extending beyond said body and terminating in an optical marker means, and the other end of said axle extending beyond said body and terminating in a plumb bob, said plumb bob being interconnected to said axle to apply a gravitational torque thereto.

In accordance with a second aspect of the present invention there is disclosed a method of making a marker to mark a patient's eyeball prior to intraocular surgery, said method comprising the steps of:
(i) locating at least two marker points one at each opposite end of a substantially U-shaped yoke,
(ii) locating said yoke at one end of an axle,
(iii) rotatably mounting said axle within a substantially co-axial hollow handle, the other end of said axle extending beyond said handle, and
(iv) connecting a plumb bob to said handle to apply a gravitational torque thereto.

BRIEF DESCRIPTION OF THE DRAWINGS

A preferred embodiment of the invention will now be described, by way of example only, with reference to the accompanying drawings in which.

DETAILED DESCRIPTION

Figure 1:
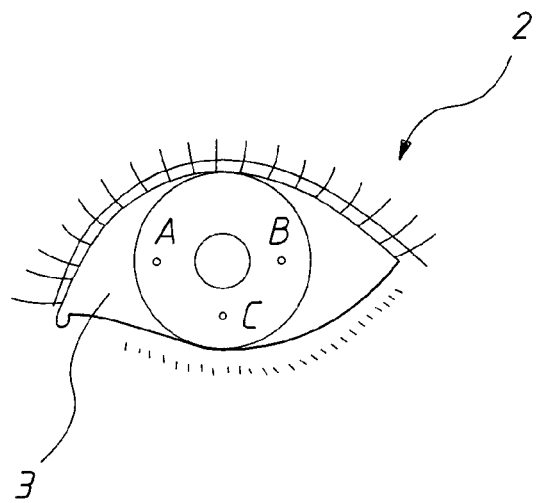
FIG. 1 is front elevational view of a patient's eye with the patient vertical and showing the desired location of three marks.

As seen in FIG. 1, prior to carrying out ophthalmic surgery, the eye 2 is required to be marked in order to enable the ophthalmic surgeon to identify the centre (or axis or front) of the eye when the patient is upright. As seen in FIG. 1 three points are preferably marked which in relation to the globe of the earth are as follows:
A: is on the equator, but at 90° west of the Greenwich meridian,
B: is also on the equator but 90° east of the Greenwich meridian, and
C: is on the Greenwich meridian but a latitude corresponding to the South Atlantic.

Figure 2:
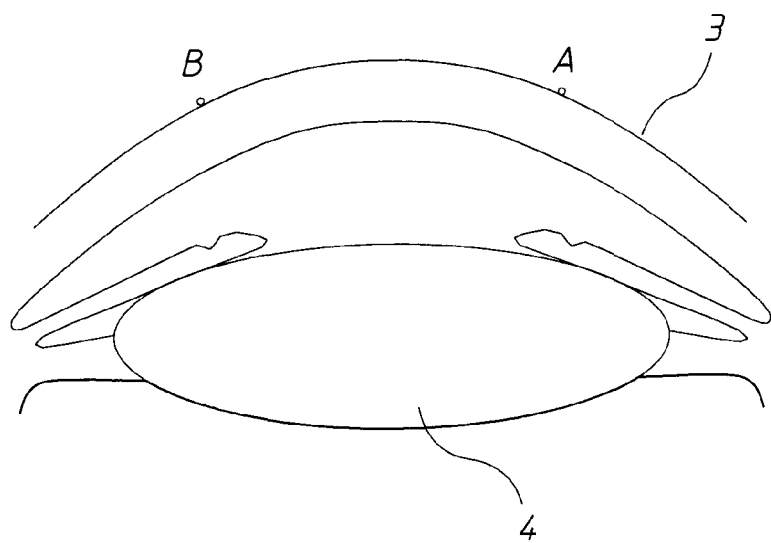
FIG. 2 is a horizontal cross-section to enlarged scale showing the patient's cornea and the marks A and B of FIG. 1.

The points A and B are also illustrated in FIG. 2 which is a cross-sectional view taken along the line A-B of FIG. 1 and thus passes through the centre of the cornea 4.

Figure 3:
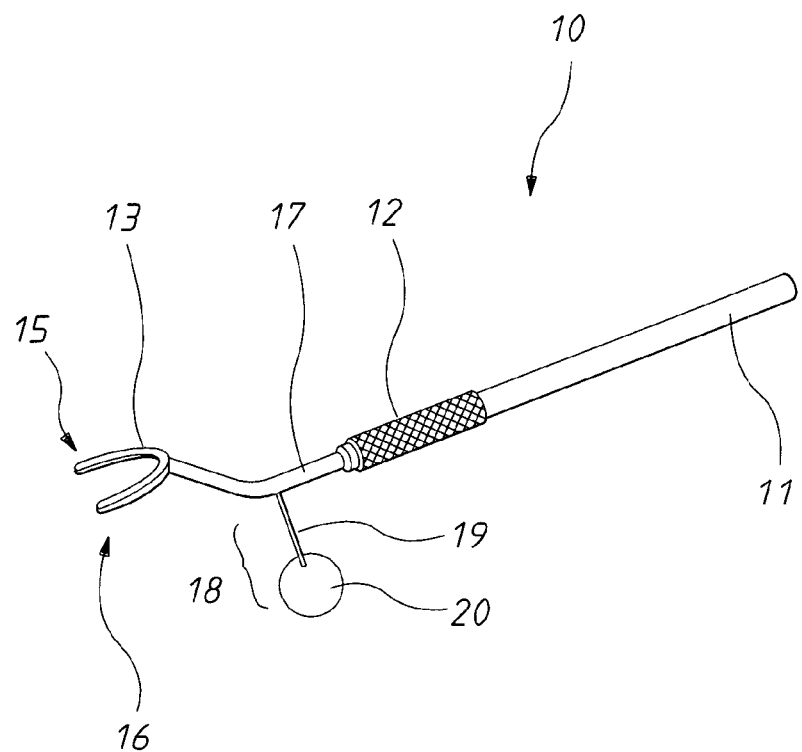
FIG. 3 is a perspective view of a prior art ophthalmic marking device.

The prior art marking device able to mark the points A and B (only) of FIG. 1 is illustrated in FIG. 3. The prior art device 10 has a pencil like handle 11 having a knurled portion 12 which enables the handle 11 to be conveniently held like a pencil by the hand of the ophthalmic surgeon.

At the front of the device 10 is a U-shaped yoke 13 having two points 15, 16 to which a dye can be applied and which when placed on the eyeball 3 create the marks A and B. The yoke 13 is connected to the handle 11 by means of a curved rod 17 which is rotatably mounted within the handle 11. A plumb bob 18 having a rigid stem 19 and a sphere 20, is rigidly connected to the rod 17.

In operation the device 10 is held with the handle 11 in a substantially horizontal plane opposite the patient's eye 2. The weight of the plumb bob 18 ensures that the rod 17 is rotated by the plumb bob 18. Thus the plumb bob 18 is vertical and so the yoke 13 (which is perpendicular to the stem 19) is horizontal. Thus provided the ophthalmic surgeon keeps the handle 11 in a substantially horizontal plane, the ophthalmic surgeon can judge the centre (or axis or front) of the eye and then bring the points 15 and 16 into contact with the eyeball 3 and thereby make the marks A and B simultaneously and reasonably accurately.

This arrangement suffers from three difficulties. The first is that the ophthalmic surgeon must keep the handle 11 substantially horizontal in order to ensure that the rod 17 can rotate under the influence of the plumb bob 18. In addition, the fingers of the ophthalmic surgeon are not able to be moved any further forwardly along the device 10 than the knurled portion 12 since the fingers must not interfere with the swinging operation of the plumb bob 18. As a consequence, the ophthalmic surgeon has only his other hand with which to control the patient's eye lids and so this is generally of inconvenience to the ophthalmic surgeon. Thirdly, the plumb bob 18 must not come into contact with the patient lest its vertical position be disturbed, thereby moving the pointers 15, 16 away from the horizontal.

Figure 4:
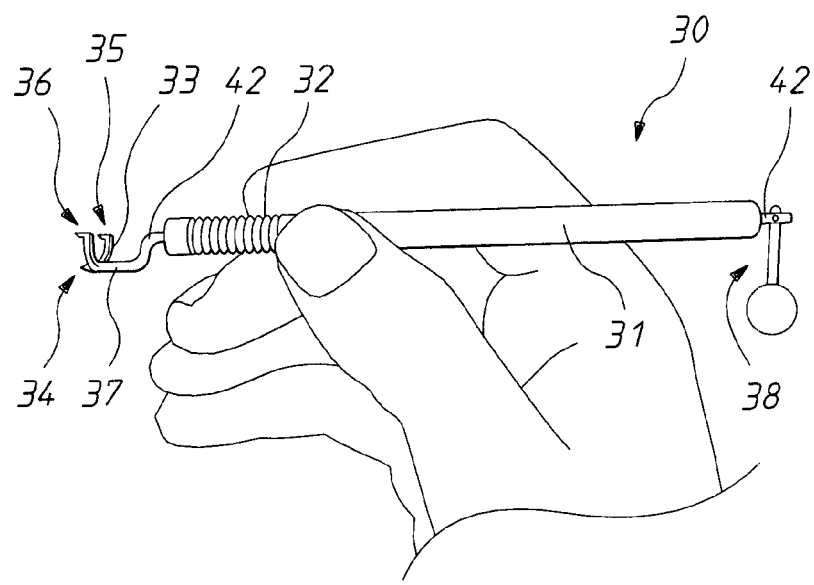
FIG. 4 is a perspective view of the ophthalmic marker of the preferred embodiment being held in the right hand of an ophthalmic surgeon.
Figure 5:
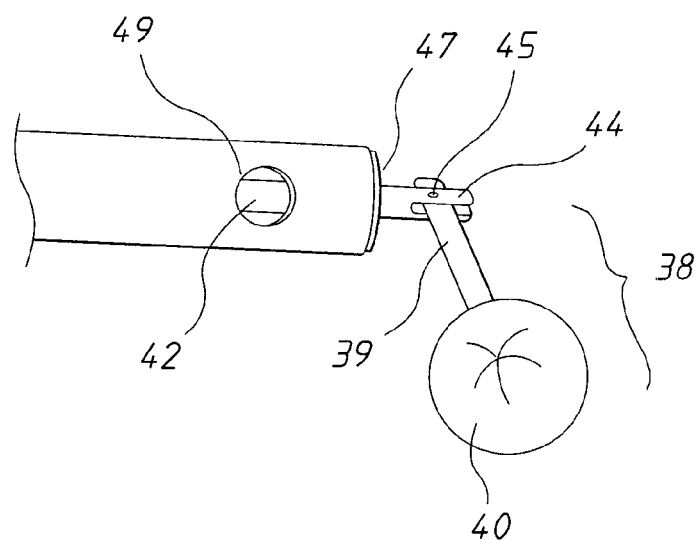
FIG. 5 is a perspective view of the rear end of the ophthalmic marker of FIG. 4.
Figure 6:
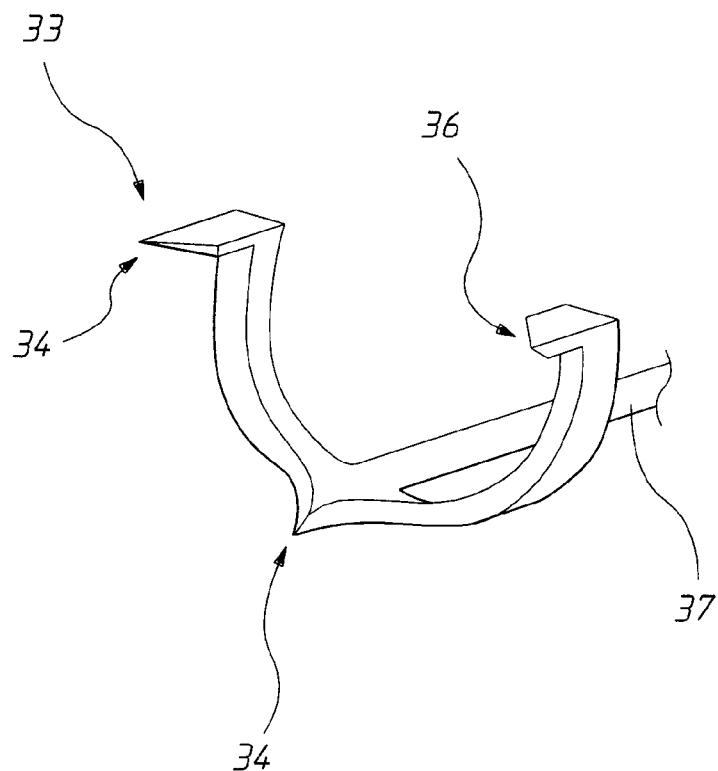
FIG. 6 is a perspective view looking towards this right of the U-shaped yoke of the ophthalmic marking device of FIG. 4.

Turning now to FIGS. 4 to 6, the ophthalmic marker 30 of the preferred embodiment has a handle 31 with a ribbed portion 32 constituting a finger grip. A U-shaped yoke 33 is provided but is orientated into the vertical plane and has three points 34, 35 and 36 respectively which protrude perpendicularly from the plane of the yoke 33. The yoke 33 is connected by means of a cranked portion 37 to an axle 42 which extends the length of the handle 31. The axle 42 is rotatably mounted relative to the handle 31 so as to be substantially co-axial therewith and to be a smooth substantially frictionless rotational fit within the handle 31.

As best seen in FIG. 5, the rear end of the axle 42 is bifurcated at 44 and the rigid stem 39 of a plumb bob 38 (including a sphere 40) is pivoted by means of a pin 45 which extends through the bifurcated portion 44 of the axle 42. As also seen in FIG. 5, the axle 42 is supported by a bearing plate 47 and is conveniently visible through an aperture 49 in the handle 31.

Since the axle 42 is rotatably mounted, the weight of the plumb bob 38 with its sphere 40 maintains the U-shaped yoke 33 with its points 35 and 36 uppermost and level (ie horizontal), irrespective of any twisting action of the handle 31 relative to the axle 42. Thus no matter how the ophthalmic surgeon either deliberately or inadvertently rotates the handle 31 relative to the axle 42, the axle 42 always remains stationery with the stem 39 vertical and thus the points 35 and 36 horizontal.

Furthermore, the handle 31 can be tilted in a vertical plane through a wide range of degrees and the plumb bob 38 remains vertical since the stem 39 is able to pivot about the pin 45. Therefore it is not necessary for the ophthalmic surgeon to keep the handle 31 in a substantially horizontal plane as is the case with the handle 11 of the prior art device 10.

As a consequence of these mechanical improvements, the marker 30 is much more convenient for the ophthalmic surgeon to use. In particular, the forefinger and middle finger of the hand holding the marker 30 are available to assist in maintaining the patient's eye lids retracted and steady the hand, if necessary, thereby enabling the ophthalmic surgeon to use more than one hand in carrying out the marking procedure.

In addition, the additional point 34 enables the mark C as illustrated in FIG. 1 to be made, thereby improving the definition of the optical axes for the surgeon.

The foregoing describes only one embodiment of the present invention and modifications, obvious to those skilled in the ophthalmic arts, can be made thereto without departing from the scope of the present invention.

The term "comprising" (and its grammatical variations) as used herein is used in the inclusive sense of "including" or "having" and not in the exclusive sense of "consisting only of".

The invention claimed is:

1. An ophthalmic marking device for marking a patient's eyeball prior to intraocular surgery, said marking device comprising a central longitudinal axle contained within, and rotatable relative to, an elongate, substantially co-axial and substantially cylindrical body constituting a pencil like handle, one end of said axle extending beyond said body and terminating in an optical marker, and the other end of said axle extending beyond said body and terminating in a bifurcated pivotable connection with a plumb bob, said plumb bob being interconnected to said axle to apply a gravitational torque thereto.

2. The marking device as claimed in claim 1, wherein said plumb bob is moveable in only a single plane relative to said axle.

3. The marking device as claimed in claim 1, wherein said plumb bob comprises a rigid stem having a bulb at its lower end.

4. The marking device as claimed in claim 3, wherein said bulb is substantially spherical.

* * * * *